US006294764B1

United States Patent
Lindner et al.

(10) Patent No.: US 6,294,764 B1
(45) Date of Patent: Sep. 25, 2001

(54) MULTI-COMPONENT PROCESS ANALYSIS AND CONTROL

(75) Inventors: Jeffrey S. Lindner, Starkville; Hossein Toghiani, Mississippi State, both of MS (US); Jason M. Hamilton, Plaquemine, LA (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 09/413,477

(22) Filed: Oct. 6, 1999

Related U.S. Application Data (60) Provisional application No. 60/103,329, filed on Oct. 7, 1998.

(51) Int. Cl.[7] .................................................. B23K 10/00
(52) U.S. Cl. .............. 219/494; 219/121.55; 219/121.54; 219/121.48; 110/250; 588/900
(58) Field of Search ........................ 219/121.54, 121.55, 219/121.57, 121.59, 121.43, 121.44, 121.48; 588/210, 212, 227, 900; 110/250, 256, 342, 246–248; 250/559.4, 574, 573

(56) References Cited

U.S. PATENT DOCUMENTS

| | | | |
|---|---|---|---|
| 5,047,612 | * 9/1991 | Savkar et al. ................... 219/121.47 |
| 5,151,474 | 9/1992 | Lange et al. ........................ 526/60 |
| 5,383,019 | 1/1995 | Farrell et al. . | |
| 5,430,295 | 7/1995 | LeFebre et al. ..................... 250/340 |
| 5,431,734 | 7/1995 | Chapple-Sokol et al. ............ 118/712 |
| 5,457,260 | 10/1995 | Holt ..................................... 585/820 |
| 5,477,048 | * 12/1995 | Nakagawa et al. ................... 250/288 |
| 5,665,608 | 9/1997 | Chapple-Sokol et al. ............... 438/7 |
| 5,665,698 | 9/1997 | Narula et al. .......................... 512/19 |
| 5,777,735 | 7/1998 | Reagen ................................. 356/346 |
| 5,912,471 | * 6/1999 | Schutz ................................. 250/574 |
| 6,153,852 | * 11/2000 | Blutke et al. ..................... 219/121.59 |

OTHER PUBLICATIONS

Hamilton, Jason Marcus, Thesis: Process Optimization Studies of a Surrogate Mixed Waste Plasma Torch Processing Facility Using Extractive FTIR Spectroscopy in an Advanced Process Control Strategy, Dec. 1998.

* cited by examiner

*Primary Examiner*—Mark Paschall
(74) *Attorney, Agent, or Firm*—Piper, Marbury, Rudnick & Wolfe; Steven B. Kelber, Esq.

(57) ABSTRACT

An apparatus and method for multiple component process analysis and control includes the steps of obtaining a sample from a process stream, interrogating the sample using spectroscopy according to an established QA/QC protocol to determine the concentrations of a plurality of molecules in the sample, transmitting the determined concentrations to a control computer, determining control system response based upon the determined concentrations and a process model, implementing at least one facility action based on the control system response, and repeating the obtaining, interrogating, transmitting, determining and implementing steps. The apparatus extends the technology of multi-component analytical instrumentation to the direct use in a controller suitable of a wide variety of processes encountered in waste remediation, chemical manufacturing, combustion, and other industrial operations.

29 Claims, 6 Drawing Sheets

MULTI-COMPONENT PROCESS ANALYSIS AND CONTROL

This application is a regular National application claiming priority from Provisional Application, U.S. application Ser. No. 60/103,329, filed Oct. 7, 1998. The entirety of that provisional application is incorporated herein by reference.

BACKGROUND OF THE INVENTION

This invention relates generally to the field of automated controls and more particularly to multi-component process analysis and control of operations within applicable industrial segments.

Compositional evaluation of industrial process streams currently involves sampling followed by laboratory evaluation. Normally, specific locations along the process stream are selected. Samples may be gathered in the exhaust stack to confirm that the facility is in permit compliance. Other evaluation points may be after specific operations or directly prior to packaging and are used to gauge process efficiency and/or product purity. One problem with this approach concerns the time lag between the actual sampling event and attainment of the desired analytical information. Sample integrity may also be a concern if deleterious reactions are possible or if chemical reactions have not proceeded to completion.

Basing decisions upon delayed-time data can lead to deficiencies in process control, especially when hours or tens of minutes are needed for the analysis. In such a situation, the process would continue to operate under the same conditions until the new sample information was received. Assuming that the chemical information was unacceptable, the plant operators would proceed to systematically change process control variables (temperatures, feed rate, etc.) until a desirable process condition was obtained. Tuning a large-scale process in this manner can be inefficient and product yields during the out-of-specification period would be lower than expected, which would translate into lost revenues (lower profit margins) and an increase in process emissions (reactant byproducts). Furthermore, once the process is tuned, slight changes in raw material feed stocks can effect product yields. These input changes would normally go unnoticed and the process would not be operating at peak efficiency.

The most appropriate means for assuring high product yields while controlling process emissions would be to rapidly determine the necessary chemical information and transmit the results to, for example, the facility control computer, wherein decisions based on a specified process model could be automatically implemented.

The use of Fourier Transform Infrared (FTIR) spectroscopy allows determination of the concentrations of multiple gas phase constituents in near real time. Simply interfacing an FTIR at appropriate facility locations, either in an extractive (sampling) or in an on-line (non-intrusive) configuration, i.e., across a process channel, followed by communication of the results is, however, insufficient. In order to produce a reliable, effective, and robust process control scheme, a system (or protocol) of instrumental and measurement guidelines and quality assurance/quality control (QA/QC), must be adopted. Without such validations system implementation can be rendered ineffective and may result in erroneous observations leading to the misapplication of controls. The use of a protocol also allows for numerous checks on the performance of the instrument and the data obtained. The concept disclosed herein is intended to eliminate the obstacles associated with the lack of a viable QA/QC plan and with other deficiencies, noted in the prior art, regarding process specificity.

Chapple-Sokol et al. (Chapple-Sokol), U.S. Pat. Nos. 5,431,734, and 5,665,608, describe a system for control of the addition of aluminum oxide to a chemical vapor deposition reactor based on the use of FTIR to detect product degradation. The technology employs an in-line analysis cell and a single valve operated to either permit the chemical to flow into the reactor or to bypass the reactor altogether if the chemical has been found to have degraded. Improved product yield is expected. However, Chapple-Sokol do not disclose or suggest quality assurance/quality control and are targeted to the evaluation of a single chemical and the associated degradation products. Application of the developed technology would be limited to gas stream temperatures consistent with preservation of the materials and components used in the sample cell.

Holt (U.S. Pat. No. 5,457,260) discusses the use of near-infrared spectroscopy to control a simulated moving absorbent bed separation process. The target application is specific and a QA/QC framework for imposing regulation on the measurements, thereby assuring the acceptability of the data, is lacking.

Le Feber et al. (U.S. Pat. No. 5,430,295) describes a process for the controlled mixing of petroleum components. The specific embodiment relies on a control process based on a specific model for the generation of the product of choice. The foremost method for detection of the specific target molecule in the mixture was noted as near-infrared spectroscopy although other means for the determination of the given molecule or final product parameter are claimed. Again, a QA/QC frame work was not considered.

Lange et al. (U.S. Pat. No. 5,151,474) describe the use of a multi-component analyzer (FTIR spectrometer) in the context of controlling a polymerization process for polyolefins. The spectrometer is directed toward the quantification of 1-octene, ethylene, and propylene. Lange et al. does not refer to a standard means for assuring and controlling the quality of the measurements. Moreover, applications to processes other than olefin polymerization were not considered.

Reagen (U.S. Pat. No. 5,777,735) describes an in-situ gas analyzer consisting of the basic functional components of an FTIR spectrometer. A traceable QA/QC protocol is cited but the gas analyzer does not consider the direct control of industrial and/or manufacturing processes. The cited invention is specific for evaluating trace concentrations in ambient air samples (there is no sample pre-processing involved), thus the objectives and scale of the instrumentation are directly applicable to the field of industrial hygiene and not process control where typically larger molecular concentrations are encountered.

SUMMARY OF THE INVENTION

The present invention overcomes the aforementioned limitations of the prior art to a great extent by providing an apparatus and method for multiple component process analysis and control comprising the steps of obtaining a sample from a process stream, interrogating the sample using Fourier transform infrared spectroscopy according to an established QA/QC protocol to determine the concentration(s) of a single or multiple constituents which indicate the state of the process, transmitting the determined concentration(s) to a control computer, determining control system response based upon the determined concentration(s)

and a process model, implementing at least one facility action based on the control system response, and repeating the obtaining, interrogating, transmitting, determining and implementing steps. Furthermore, the MPAC system extends the technology of multi-component analytical instrumentation to direct use in a controller suitable of a wide variety of processes encountered in waste remediation, chemical manufacturing, combustion, and other industrial operations.

An object of the invention is to provide an automated controller which is based upon a method suitable for quantification of multiple components inherent to a process stream sample coupled with a viable and traceable quality assurance/quality control (QA/QC) routine thereby permitting rapid temporal quantification of multiple components enabling a high level of process control.

Another object of the invention is to provide a control system that is versatile enough so as not to be restricted to a specific application.

Another object of the invention is to provide a controller which allows for incorporation of various control scheme architectures.

A further object of the invention is to provide a control system based upon reliable technology.

Yet another object of the invention is to provide a control system capable of increasing product yields as opposed to traditional control systems.

Still yet another object of the invention is to provide a control system which can be used to limit and control environmental impact.

Another object of the invention is to provide a control system which will improve process efficiencies, thereby decreasing operating costs.

Another object of the invention is to provide a control system which completely documents process conditions.

A further object of the invention is to provide a control system that provides the operator with direct knowledge, on a time scale of better than 15 seconds, of environmental impact, product distribution and yield.

Another object of the invention is to provide a plasm torch assembly including multiple gas sources and a controller that automatically controls the gas composition directed to a plasma arc based on the concentrations of exhaust gas from the torch.

In another embodiment of the invention, positive pressure is used to route the sample to the sample manifold.

In other embodiments of the invention, alternative spectroscopic methods, capable of multi-component quantification, i.e. Raman, near-infrared, and absorption spectroscopy, (with or without laser excitation) are employed.

In preferred embodiments, a single computer is used for operation of the target spectroscopic-based system and the controller.

Other objects, aspects and advantages of the present invention will become apparent from the following descriptions, taken in connection with the accompanying drawings, wherein, by way of illustration and example, an embodiment of the present invention is disclosed. It is to be understood that in some instances various aspects of the invention may be shown exaggerated or enlarged to facilitate an understanding of the invention.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
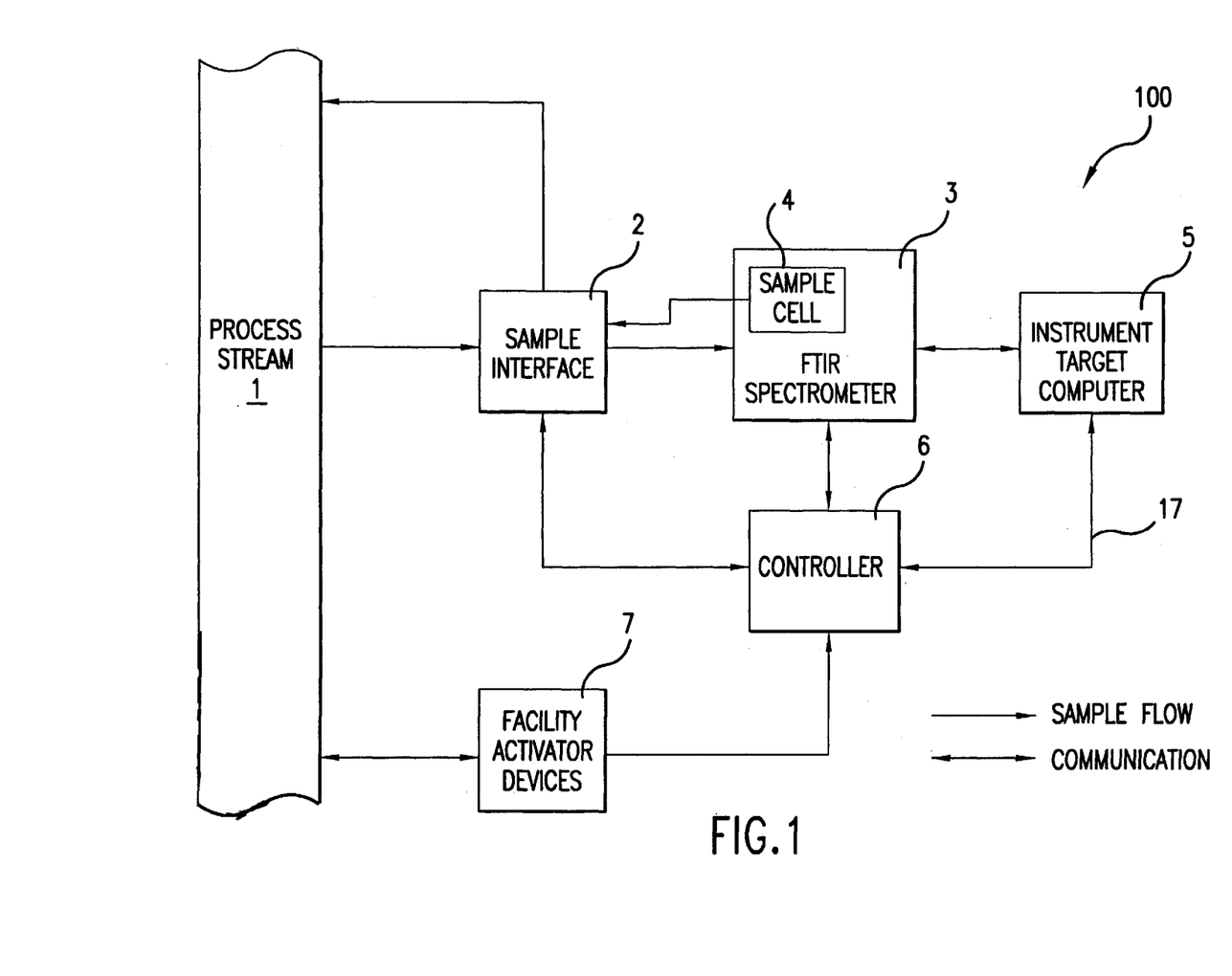
FIG. 1 is a block diagram of the multi-component process analyzer and controller.

Referring now to the drawings, wherein like reference numerals designate identical or corresponding parts throughout the several views, and most particularly to FIG. 1, a multi-component process analyzer and controller (referred to herein as an "MPAC") 100 according to a preferred embodiment of the present invention is illustrated in block diagram form. In the MPAC 100, the sample interface 2 extracts a portion of a process stream 1 under the control of the controller 6. The sample interface 2 may also condition the sample according to the prior art depending on the sampling location with respect to the flow stream. The extracted portion of the process stream is conveyed to the sample cell 4 of an FTIR spectrometer 3, the latter item being configured in the mid-IR portion of the electromagnetic spectrum in a preferred embodiment. After interrogation by the FTIR spectrometer 3, the sample may be exhausted into the process stream 1 downstream from where the sample was originally collected, or alternately directed to disposal.

The FTIR spectrometer 3 is controlled by an automated program within the instrument target computer 5 that is activated according to a prescripted sequence in the software of the controller 6. The software in the instrument target computer 5 controls the spectral and temporal resolution of the interferometer, the processing of all of the spectral data and determination of the statistical quantities pertinent to the QA/QC protocol, the calculations of the concentrations of the molecules in the process sample (or calibration transfer standard) by recourse to calibration methods known in the prior art, archiving of the data with the associated measurement time stamp, and the transmission of the pertinent results, i.e. concentrations, time stamp, and status flags to the controller 6. In preferred embodiments, the protocol followed is the EPA protocol entitled "Protocol for the Use of Extractive Fourier Transform Infrared (FTIR) Spectrometry for the Analysis of Gaseous Emissions From Stationary Sources," dated Feb. 3, 1995, the contents of which are is incorporated by reference herein. The controller 6 operates the sample interface 2, initiates data collection and analysis, and actuates the facility activation devices 7 based upon a process model.

Figure 2:
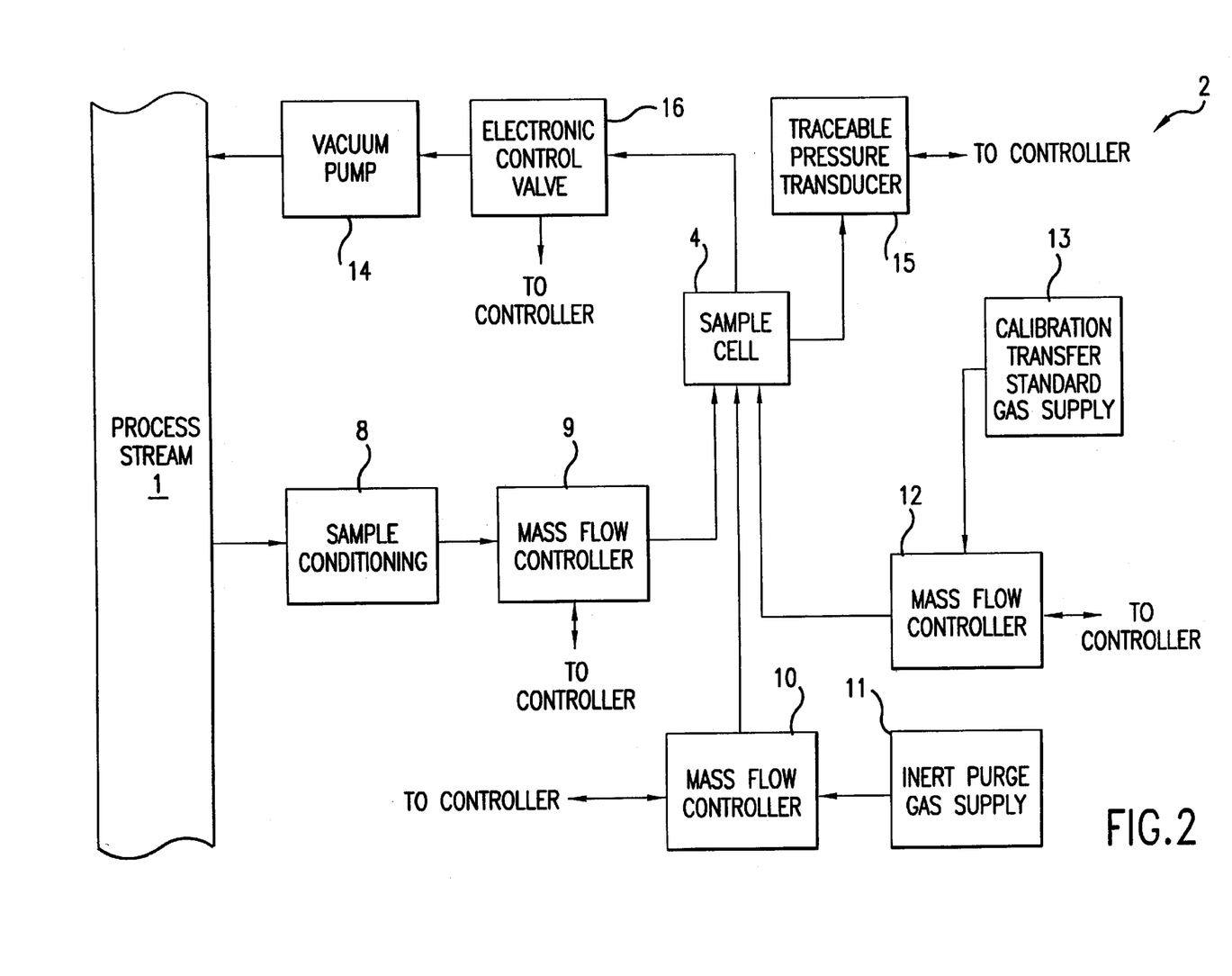
FIG. 2 is a block diagram of the sample interface illustrating the flow of the analysis stream through the various components.

The sample interface 2 is illustrated in detail in FIG. 2. A portion of the process stream 1 is optionally conditioned according to known practice (e.g., heating) in chamber 8 and then routed to the mass flow controller 9. Two additional mass flow controllers 10, 12 are employed for metering the introduction of the inert purge gas supply 11 (mass flow controller 10) and the calibration transfer standard gas supply 13 (mass flow controller 12). The inert purge gas supply 11 is a supply of inert gas which is used to flush the FTIR cell after a sample is interrogated to ensure remnants of a previous sample do not corrupt a sample. The calibration transfer standard gas supply 13 is a supply of gas of known composition and concentrations that is used to check calibration of the FTIR spectrometer 3. The calibration of the spectrometer 3 is checked both before and following the time period where samples from the facility are evaluated in a preferred embodiment.

The portion of the process stream 1, the inert purge gas supply 11, or the calibration transfer standard gas supply 13, depending upon the particular operation required, is conveyed to the sample cell 4 of the spectrometer 3, where analysis of the sample using infrared absorption spectroscopy takes place. A vacuum pump 14 supplies the suction necessary for maintaining a constant flow through the system (those of skill in the art will recognize that the vacuum pump 14 may not be necessary where there is a sufficient positive pressure in the process stream 1). The pressure of the system is monitored with a pressure transducer 15 that is traceable to the National Institute of Standards and Technology NIST). The pressure and temperature of the system are maintained at the same values used during calibration of the system according to the protocol. The pressure is controlled by the electronic control valve 16, also under the control of the controller 6.

Figure 3:
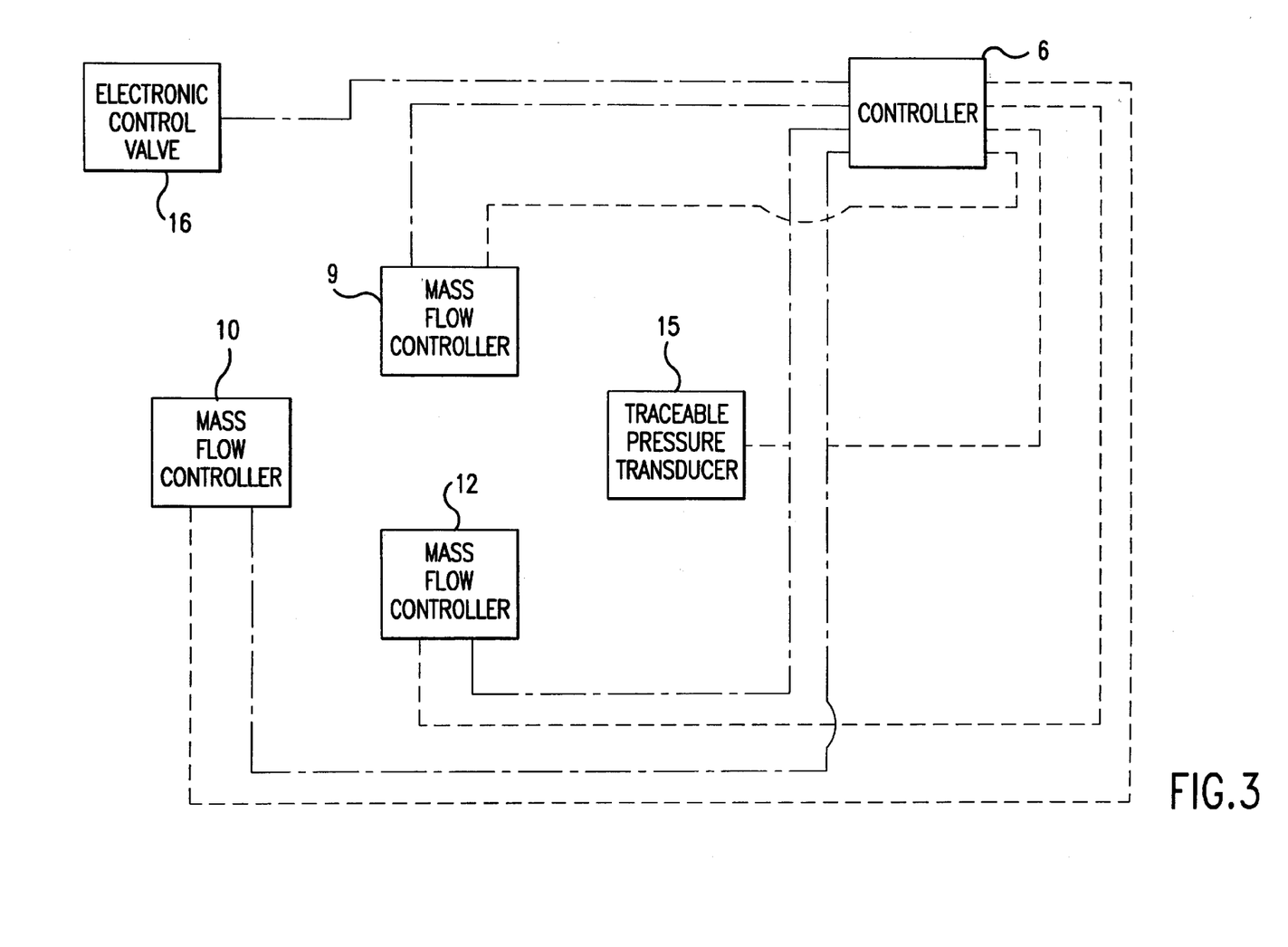
FIG. 3 illustrates the communication lines between the sample interface and the controller.

FIG. 3 illustrates the interconnection of the mass flow controllers 9, 10, 12, the electronic control valve 16, and the traceable pressure transducer 15 to the controller 6. FIG. 3 documents the control of the sample interface components from controller 6 (dash-dot line) and polling of the valve positions (dash lines) of the mass flow controllers and the electronic control valve by the controller 6. The state and value of control of the various components is established according to the predetermined measurement sequence including any actions necessary to maintain safe system operation.

Referring back to FIG. 1, electronic communications between controller 6 and the instrument target system computer 5 are performed using two way communication over a standard interface 17 in preferred embodiments. A number of different communication options between the controller 6 and the facility actuator devices 7 are possible based on the specific configuration of the given facility control device. More connections than those illustrated may be required depending on the specific process under control and the actual number of facility actuator devices.

Figure 4:
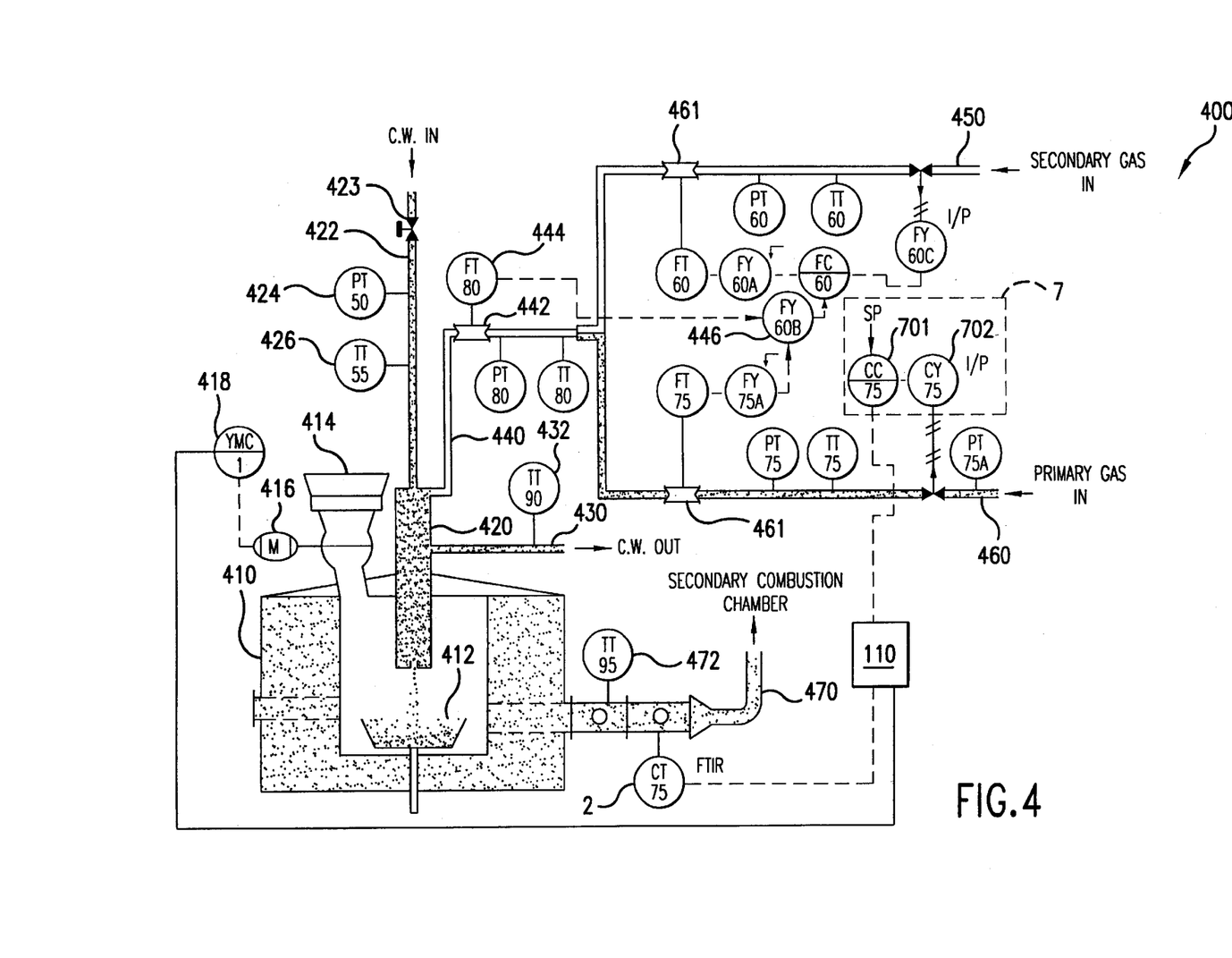
FIG. 4 is a process instrumentation diagram for control of the gas feed to a plasma torch.

The systems described in the drawings, along with the specific instruction software, constitute the major components of a machine for multi-component process analysis and control. An embodiment 400 of the invention constructed for controlling a gas composition directed to a plasma torch 420 located in an appropriate furnace 410 and processing a mixed-waste composition is shown in FIG. 4. This cited example is simply an indication of the use of the MPAC invention as a control system. In this regard it should be noted that other processes can be controlled using the technology but basing the appropriate decisions on other molecules that can be quantified using the FTIR technique. In fact, other instruments suitable for multi-component quantification could be used.

The plasma torch 420 heats the components of a waste stream to an elevated temperature either through direct interaction of the waste with the generated plasma arc or through the high temperatures that will exist in the furnace 410 through radiation transfer. Organic molecules in the mixed radioactive waste would preferentially be destroyed through radical reactions, whereas melt forming molecules and atoms would tend to liquify and then form a slag or glass in the bottom of the furnace. The ability to control the gas feed to the torch, whether nitrogen, air, or a combination thereof, will dictate the extent of destruction of the organic molecules originally present in the waste and the formation of deleterious polluting and greenhouse gases. These later molecules may arise directly from chemical reactions within the plasma and/or from the interaction of the arc with the waste.

The plasma torch employed for these experiments normally operates with the torch gas supply pressure cycling, or oscillating, in order to keep the arc attachment point on the rear plasma electrode moving to different spatial locations; thereby wearing the electrode evenly over time. This particular illustration, where the MPAC is used to control an oscillating process parameter (the gas supply pressure), is an extreme example of the control that can be attained by the system. Other processes where the control would be enacted through the operation of feeders, mixers, or through the control of temperature, flow or pressure, or a combination thereof, would not be as involved.

In the embodiment 400 shown in FIG. 4, the waste, in the form of briquettes, is routed to the torch furnace 410 using a feeder 414, which passes the briquettes into a crucible 412 on the floor of the furnace 410. The feeder 414 is driven by a motor 416, which is controlled by a motor control 418. In the particular embodiment 400 illustrated in FIG. 4, the feeder 414 is a screw-type feeder, which may be set to one of two possible delivery rates. Different rates were obtained by periodically activating and deactivating the feeder 414 under the control of the controller 6 (the connection between the controller 6 and the motor control 418 is not shown in FIG. 4) to obtain a desired semi-continuous rate. The control methods used to control the feeder 414 are well known in the art.

The waste material in the 412 is subjected to a plasma torch 420. The temperature of the plasma torch 420 is regulated by water supplied by the cooling water supply 422 and expelled through the drain 430. The pressure and temperature of water in the cooling water supply 422 is measured by the pressure sensor/Transmitter (S/T) 424 and temperature sensor S/T 426. The temperature of the cooling water drain 430 is measured by the temperature S/T 432 sensor 432. The input from the S/T's 422, 424, 432 are used to monitor the plasma torch operating temperature, but no control function is performed in this embodiment.

As the plasma torch 420 burns the briquettes, the resulting gases are passed to a secondary combustion chamber (not shown in FIG. 4) through exhaust 470. The temperature of the exhaust gas is measured by the temperature S/T 472. An exhaust gas sample, which will be analyzed using FTIR spectroscopy, is extracted (and returned downstream) at sample interface 2, and the analysis result is converted and transmitted to 7011 (CC-75) in controller 6.

The gas supplied to the plasma torch 420 is either air (the primary gas), nitrogen (the secondary gas), or a combination of both. Intuitively, large levels of carbon monoxide CO and correspondingly low levels of carbon dioxide $CO_2$ would be formed when waste containing organic constituents would be processed using a nitrogen plasma. Alternately, high levels of NO and $NO_2$ would be generated with operation of the torch using an air plasma. These constituents would have a tendency to be generated in direct proportion to the amounts of oxygen and nitrogen in the gas supplied to the torch 420 (and to any partitioning that would occur with the plasma constituents and the waste routed to the furnace). By using a combination of air and nitrogen to supply the torch 420, it is possible to keep the carbon monoxide CO concentration in the exhaust gas at an acceptable level while reducing the $NO_x$ output as compared to supplying air alone to the torch.

The process instrumentation diagram (FIG. 4) was developed based upon this intuitive model. Detection of a CO level above a specific threshold can be used to instigate controller action, this is, to control the composition of the torch gas (by increasing the oxygen content) to reduce the CO level to an acceptable level while reducing the formation of NO and $NO_2$ (as compared to an air plasma). In automatically performing these actions, a controller could be used for achieving a high organic destruction efficiency while still minimizing the environmental impact of $_{Nox}$.

There are two control loops in the gas supply system. Controller 6, which comprises concentration controller CC-75 and flow controller FC-60, controls each of the two loops. The first control loop controls the flow rate of the primary gas 460. In the first control loop, the CO concentration transmitter CT-75 transmits the concentration of carbon monoxide obtained from the FTIR to the concentration controller CC-75. The concentration controller CC-75 compares the measured concentration of CO with its setpoint (SP) and manipulates the primary gas supply accordingly by transmitting an electrical signal to the I/P (current to pressure) transducer CY-75, which in turn controls a fail-open hydraulic valve 469. Manipulating the primary gas supply 460 is an example of a facility action.

The second loop is a flow loop which controls the flow rate of the secondary gas 450. The flow element 461 (comprising a venturi meter) and differential pressure transducer FT-75 measure the flow rate of the primary gas 460 and transmit a representative signal through the square root extractor FY-75A to a calculation block FY-60B. Similarly, a flow element 442 and differential pressure transducer FT-75 measure the total flow rate of the combined primary and secondary gases and transmit a representative signal through the square root extractor FY-80A to the calculation block FY-60B. The calculation block FY-60B determines the desired secondary gas flow rate based upon the measured primary gas flow rate, the measured total gas flow rate and the desired total gas flow rate (note: the total gas flow rate must be oscillated to prolong the life of the electrode in the plasma torch 420 as discussed above). The calculation block FY-60B then transmits the desired secondary gas flow rate—the set point for the secondary gas—to the flow controller FC-60. The flow controller FC-60 then compares the set point with the actual flow rate of the secondary gas supply 450 as measured by the flow element 451 and differential pressure transducer FT-60 and transmitted through the square root extractor FY-60A. The flow controller FC-60 then controls a valve 459 through the I/P transducer FY-60C. Those of skill in the art will recognize that the choice of AIR as the primary gas and nitrogen as the secondary gas could be reversed.

A first set of experiments were performed to establish the concentration levels of the targeted molecules when the plasma was generated form nitrogen and then from air and where the pressure of the gas supplied to the torch was held constant. An average $CO_2$ concentration of 33,400±790 ppm was found for the nitrogen plasma case with a surrogate waste feed of 5 briquettes per minute. Under these conditions the average NO concentration was 350±30 ppm and time-averaged. $NO_2$ and $H_2O$ concentrations were determined as 30±4 ppm and 840±110 ppm. At this same waste introduction rate, the use of a plasma generated from air yielded an average $CO_2$ concentration of 182,580±4,200 ppm. (The increase in the amount of $CO_2$ obtained with the air plasma as compared to the nitrogen plasma signifies a corresponding decrease in the amount of CO obtained with the air plasma relative to the nitrogen plasma.) With the air plasma, the concentrations of NO, $NO_2$, and $H_2O$ increased to 4040±371 ppm, 770±70 ppm, and 9670±980 ppm, respectively.

In practice, an oscillating gas flow drives the plasma as discussed above. Experiments where the MPAC invention was employed indicated an average $CO_2$ concentration, for three separate runs, of 66,290±1,530 ppm. This represented a 50% increase of $CO_2$ as compared to the control runs where nitrogen was the source gas for the torch, and a 64% decrease as compared to operation with an air plasma. During the same runs, NO concentration averaged 1,830±170 ppm, representing an 81% increase over the nitrogen-based plasma. On the other hand, NO concentration decreased by 55%, as compared to that of the control experiments with air feed to the torch. The same general trends were observed for the $NO_2$ and $H_2O$ concentrations. Average $NO_2$ and $H_2O$ concentrations of 70±10 ppm and 1,200±110 ppm, respectively, were observed. The average $NO_2$ concentration represents a 54% increase over that value obtained for the nitrogen baseline case and the concentration of water corresponds to a 91% decrease as compared to the air plasma.

Figure 5:
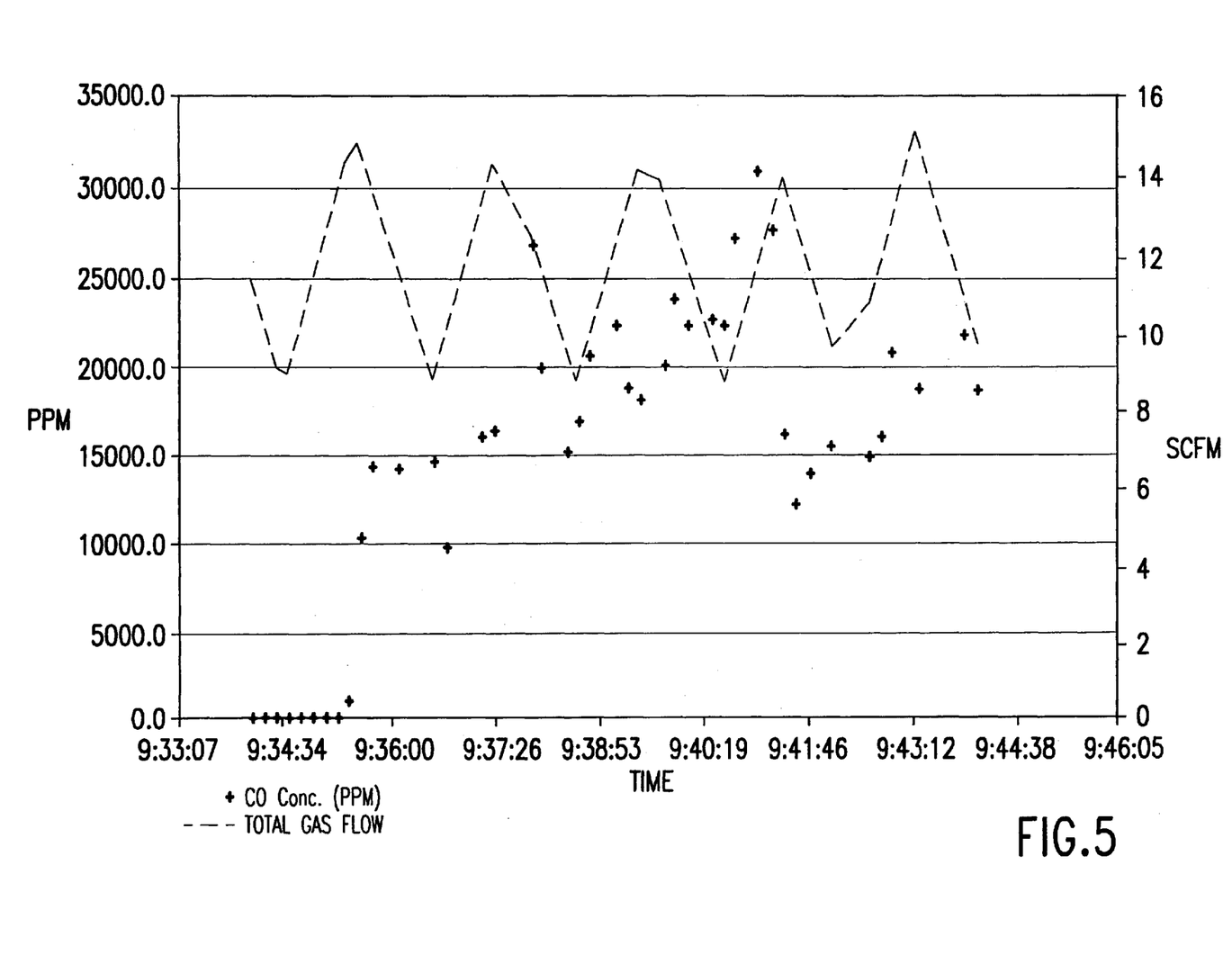
FIG. 5 is a plot of the gas flow to the plasma torch and the CO concentration level when the gas routed to the torch was nitrogen (baseline case) and when surrogate waste was injected into the torch furnace.
Figure 6:
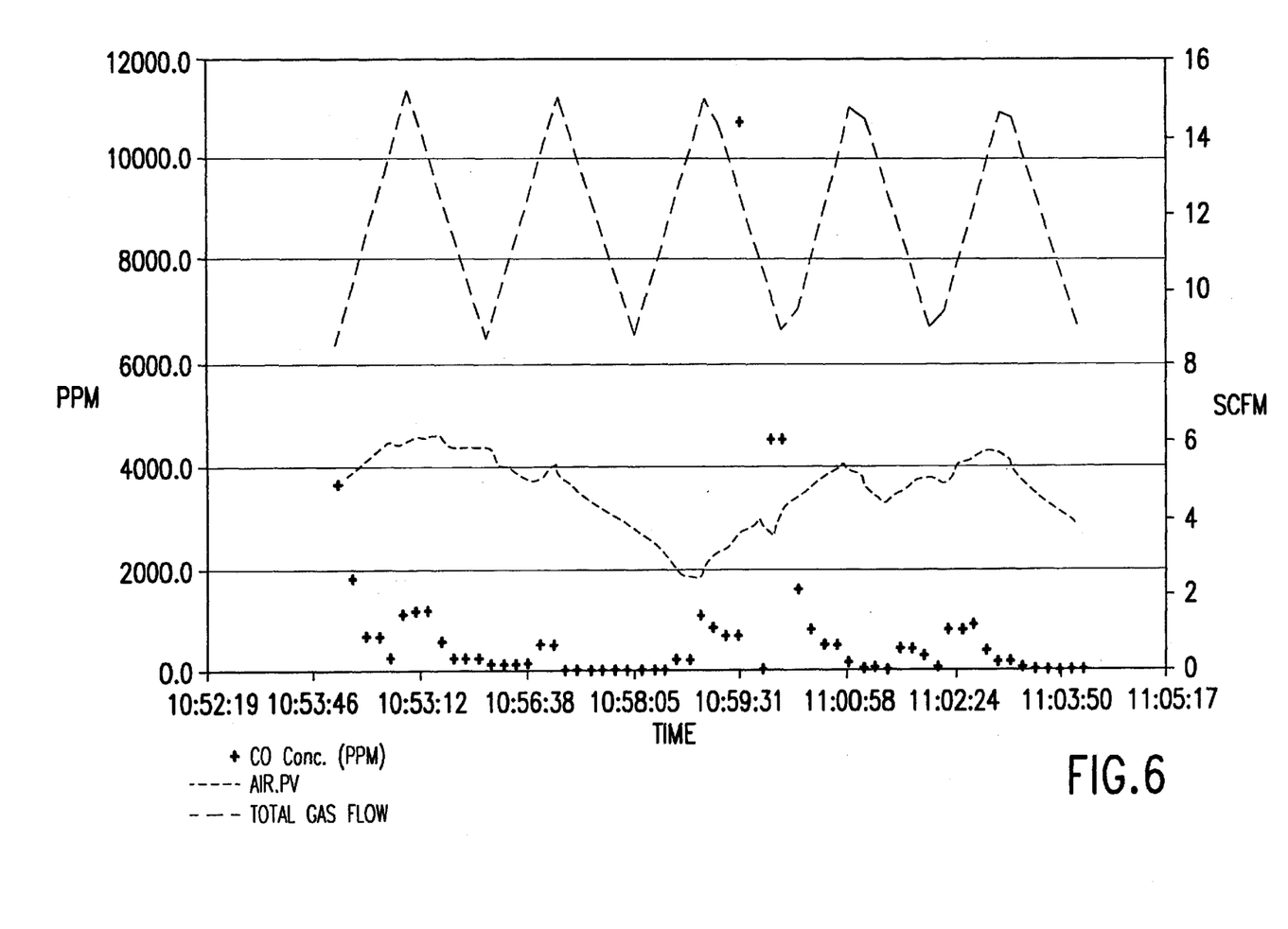
FIG. 6 illustrates the total gas flow to the plasma torch, that portion of the total gas flow from air, and the levels of CO when the surrogate waste was directed to the torch furnace and the process was under direct control using an embodiment of the invention.

Contrasts of the results for CO obtained during the nitrogen plasma experiments and during the experiments where the torch gas composition was varied by the invention, both corresponding to cycling the pressure of the gas fed to the plasma torch, and illustrated in FIGS. 5 and 6. CO concentrations measured using the system where the plasma torch was operated on $N_2$ gas average roughly 20,000 ppm. Of interest in FIG. 6 is the variation of the CO concentrations under direct control, i.e. with gas mixing according to the process model using the MPAC invention. Specifically, the CO concentrations along with the total gas flow and the flow of the air which represents a portion of the total gas flowing to the plasma torch are detailed. Note that at 10:54:09 the CO concentration is ca. 3800 ppm. The MPAC recognized that the concentration was above the threshold value and began to increase the ratio of air in the total flow to the plasma torch. The result of this increase of air was a decrease in the CO concentration at the next sampling interval indicating that the system was controlling the gas composition and thus the destruction of the surrogate waste and the impact of the process. The controller continued to vary the fraction of air in the total torch gas feed, the balance of which consisted of $N_2$, as the CO concentration increased or decreased. The air fed to the plasma torch is observed to increase as the level of CO increases and decrease as the level of CO decreases indicating direct control of the process.

An average $CO_2$ concentration of 63,410±1,460 ppm was recorded for still another set of three experimental runs using the MPAC invention. This represented a 47% increase as compared to the $N_2$ torch gas control runs, and a 65% decrease as compared to the pure air plasma run. During the same runs, NO concentration averaged 2,140±190 ppm, representing an 84% increase over that determined during operation with the $N_2$-based plasma. On the other hand, the $NO_2$ concentration decreased by 47%, as compared to that of the pure air plasma and average $NO_2$ and $H_2O$ concentrations of 10±2 ppm and 1,500±110 ppm, respectively, were observed. The average $NO_2$ concentration corresponded to a slight decrease as compared to operation of the torch on nitrogen, and a large (98%) decrease as compared to operation with a plasma based on air. The average $H_2O$ concentration corresponded to a 55% increase as compared to that of that obtained with the plasma based on nitrogen and an 85% decrease as compared to that determined when the gas routed to the torch was air.

These results indicated that the MPAC invention controlled the air and nitrogen gas fractions directed to the plasma torch (and thus the composition of the plasma) and the resulting chemistry of the process stream. The system was responsible for a decrease in the environmental impact of the process (lower $NO_x$ and CO levels) as compared to operation of the torch with an air-based plasma, and also minimized the average level of $CO_2$ while maintaining a higher organic waste destruction efficiency than if the torch was operated on nitrogen gas alone.

This invention has been described in detail in the masters thesis entitled "Process Optimization Studies of a Surrogate Mixed Waste Plasma Torch Processing Facility Using Extractive FTIR Spectroscopy in an Advanced Control Strategy" by Jason Marcus Hamilton, the contents of which are hereby incorporated by reference herein.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method for process control comprising the steps of:
    obtaining a sample from a process stream;
    interrogating the sample using spectroscopy according to an established quality assurance/quality control (QA/QC) protocol to determine the concentration of at least one constituent in the sample;
    transmitting the determined concentration to a controller;
    determining control system response based upon the determined concentration and a process model;
    implementing at least one facility action based on the control system response;
    repeating the obtaining, interrogating, transmitting, determining and implementing steps.

2. The method of claim 1, further comprising the step of heating or maintaining the sample at an elevated temperature prior to the interrogating step.

3. The method of claim 1, wherein the obtaining step is performed by extracting a portion of the process stream by vacuum.

4. The method of claim 1, further comprising the step of purging a sample cell associated with a spectrometer used in the interrogating step.

5. The method of claim 4, further comprising the step of calibrating the spectrometer using a calibration transfer standard prior to performing the repeating step.

6. The method of claim 1, further comprising the step of compiling statistical data based on results from the interrogating step.

7. The method of claim 1, further comprising the step of maintaining the sample in a sample cell having a workable volume at a temperature between approximately 120 degrees centigrade and 150 degrees centigrade.

8. The method of claim 7, wherein the sample is kept at a temperature that varies by no more than five degrees centigrade.

9. The method of claim 8, wherein the temperature varies by no more than one degree centigrade.

10. The method of claim 1, further comprising the step of returning the sample to the process stream at a location downstream from where the sample was obtained.

11. The method of claim 1, wherein the control system response is determined according to a feedback model.

12. The method of claim 1, wherein the control system response is determined according to a feed-forward, cascade or ratio control.

13. The method of claim 1, wherein the spectroscopy is infrared spectroscopy.

14. The method of claim 1, wherein the spectroscopy is Fourier transform infrared spectroscopy.

15. The method of claim 1, wherein the spectroscopy is near-infrared.

16. The method of claim 1, wherein the spectroscopy is Raman.

17. The method of claim 1 wherein measurements are made in the ultra-violet/visible portion of the electromagnetic spectrum.

18. A method for operating a plasma torch, the method comprising the steps of:
    supplying a plasma torch with at least a first gas having a first flow rate and a second gas having a second flow rate, the first gas being different fromthe second gas;
    obtaining an exhaust gas sample produced the plasma torch;
    interrogating the sample to determine the concentration of at least one constituent of the exhaust gas;
    transmitting the concentration to a controller;
    adjusting the supply of at least one of the first gas and the second gas based on the concentration; and
    repeating the obtaining, interrogating, transmitting and adjusting steps.

19. The method of claim 18, wherein the first gas is oxygen and the second gas is nitrogen.

20. The method of claim 19, further comprising the step of oscillating a total gas flow rate, wherein the total gas flow rate comprises the first flow rate of the first gas and the second flow rate.

21. The method of claim 20, wherein the interrogating step is performed according to an established QA/QC protocol.

22. The method of claim 21, wherein the interrogating step is performed using spectroscopy.

23. The method of claim 22, wherein the spectroscopy is Fourier transform infrared spectroscopy.

24. An apparatus for controlling an industrial process, the apparatus comprising:
    a sample extraction interface, said interface connectable to a process stream to obtain a sample;
    a spectrometer including a sample cell connected to the sample extraction interface to receive a sample from the sample extraction interface;
    an instrument target analyzer connected to the spectrometer to process spectra obtained from the spectrometer and determine concentrations of at least two components of the sample;

a facility activator device connectable to the process stream; and a controller connected to the sample extraction interface, the spectrometer, the instrument target analyzer and the facility activator device for controlling the sample extraction interface to extract the sample and place it in the sample cell, controlling the spectrometer to interrogate a sample in the sample cell, controlling the target instrument controller to determine the concentrations of at least two components of the sample, and controlling the facility activator device to perform a facility action based on the determined concentrations.

25. The apparatus of claim 24, wherein the sample extraction interface comprises a first mass flow controller connected to the process stream and the sample cell.

26. The apparatus of claim 25, wherein the sample extraction interface further comprises:

a purge gas supply;

a second mass flow controller connected to the purge gas supply and the sample cell;

a calibration standard gas supply;

a third mass flow controller connected to the calibration standard gas supply and the sample cell.

27. The apparatus of claim 26, wherein the first, second and third mass flow controllers are connected to the sample cell via a three way valve, the valve being configurable to a first position in which the first mass flow controller is in fluid communication with the sample cell, a second position in which the second mass flow controller is in fluid communication with the sample cell, and a third position in which the third mass flow controller is in fluid communication with the sample cell.

28. The apparatus of claim 24, further comprising a vacuum pump in fluid communication with the sample cell through a valve.

29. The apparatus of claim 24, further comprising a pressure transducer.

* * * * *

UNITED STATES PATENT AND TRADEMARK OFFICE
CERTIFICATE OF CORRECTION

PATENT NO. : 6,294,764 B1  Page 1 of 1
DATED : September 25, 2001
INVENTOR(S) : Jeffrey S. Lindner et al.

It is certified that error appears in the above-identified patent and that said Letters Patent is hereby corrected as shown below:

Title page,
Before the "References Cited" section, please insert the following:

-- This invention was made with U.S. Government support under contract number DE-FG02-93CH10575 awarded by the Department of Energy. The U.S. Government may have certain rights in this invention. --

Signed and Sealed this

Fifth Day of March, 2002

*Attest:*

JAMES E. ROGAN
*Attesting Officer*  *Director of the United States Patent and Trademark Office*